(12) United States Patent
Bala

(10) Patent No.: US 11,147,897 B2
(45) Date of Patent: Oct. 19, 2021

(54) STERILIZATION PROCESS CHALLENGE DEVICE

(71) Applicant: American Sterilizer Company, Mentor, OH (US)

(72) Inventor: Harry Bala, South Barrington, IL (US)

(73) Assignee: American Sterilizer Company, Mentor, OH (US)

(*) Notice: Subject to any disclaimer, the term of this patent is extended or adjusted under 35 U.S.C. 154(b) by 226 days.

(21) Appl. No.: 15/946,928

(22) Filed: Apr. 6, 2018

(65) Prior Publication Data

US 2019/0307910 A1 Oct. 10, 2019

(51) Int. Cl.
| | | |
|---|---|---|
| *A61L 2/28* | (2006.01) | |
| *A61L 2/07* | (2006.01) | |
| *A61L 2/02* | (2006.01) | |
| *A61L 2/20* | (2006.01) | |

(52) U.S. Cl.
CPC .............. *A61L 2/28* (2013.01); *A61L 2/022* (2013.01); *A61L 2/07* (2013.01); *A61L 2/206* (2013.01); *A61L 2/208* (2013.01); *A61L 2202/122* (2013.01); *A61L 2202/26* (2013.01)

(58) Field of Classification Search
CPC ... A61L 2/28; A61L 2/022; A61L 2/07; A61L 2/206; A61L 2/208; A61L 2202/122; A61L 2202/26
USPC .............................................................. 436/1
See application file for complete search history.

(56) References Cited

U.S. PATENT DOCUMENTS

| | | | |
|---|---|---|---|
| 4,154,342 A * | 5/1979 | Wallace | B65D 51/1616 206/439 |
| 4,853,013 A * | 8/1989 | Rio | B01D 36/001 96/6 |
| 5,866,356 A * | 2/1999 | Albert | A61L 2/28 422/416 |
| 5,955,296 A * | 9/1999 | Roll | C12Q 1/22 435/287.4 |
| 6,391,541 B1 * | 5/2002 | Petersen | B01L 3/502 435/5 |
| 7,247,482 B2 | 7/2007 | Lemus et al. | |
| 7,718,125 B2 | 5/2010 | Bala | |
| 7,790,105 B2 | 9/2010 | Bala | |
| 7,875,239 B2 | 1/2011 | Bancroft | |

(Continued)

FOREIGN PATENT DOCUMENTS

| | | |
|---|---|---|
| EP | 0433053 A1 | 6/1991 |
| EP | 1201255 A2 | 5/2002 |

OTHER PUBLICATIONS

International Search Report and Written Opinion issued by ISA/EPO in connection with PCT/US2019/025994 dated Jul. 10, 2019.

(Continued)

*Primary Examiner* — Matthew D Krcha
*Assistant Examiner* — Jacqueline Brazin
(74) *Attorney, Agent, or Firm* — Levenfeld Pearlstein, LLC

(57) ABSTRACT

A sterilization process challenge device configured to test the efficacy of a sterilization process includes a tubular body for containing at least one sterilization indicator and a filter assembly including at least one filter member. The only flow path into the interior of the tubular body containing at least one sterilization indicator is provided through the filter assembly to control and restrict flow of a gaseous sterilization medium from an external environment.

15 Claims, 4 Drawing Sheets

(56) References Cited

U.S. PATENT DOCUMENTS

| | | |
|---|---|---|
| 8,486,691 B2 | 7/2013 | Larson et al. |
| 9,017,994 B2 | 4/2015 | Franciskovich et al. |
| 2013/0230910 A1 | 9/2013 | Christensen et al. |
| 2015/0231628 A1* | 8/2015 | Nozaki ............... A01N 1/0242 |
| | | 422/547 |
| 2015/0335777 A1 | 11/2015 | Robbins et al. |
| 2016/0103043 A1* | 4/2016 | Skarping ............. G01N 33/538 |
| | | 436/501 |
| 2017/0304476 A1* | 10/2017 | Taggart .................... A61L 2/22 |

OTHER PUBLICATIONS

International Preliminary Report on Patentability issued by ISA/EPO in connection with PCT/US2019/025994 dated Oct. 6, 2020.

* cited by examiner

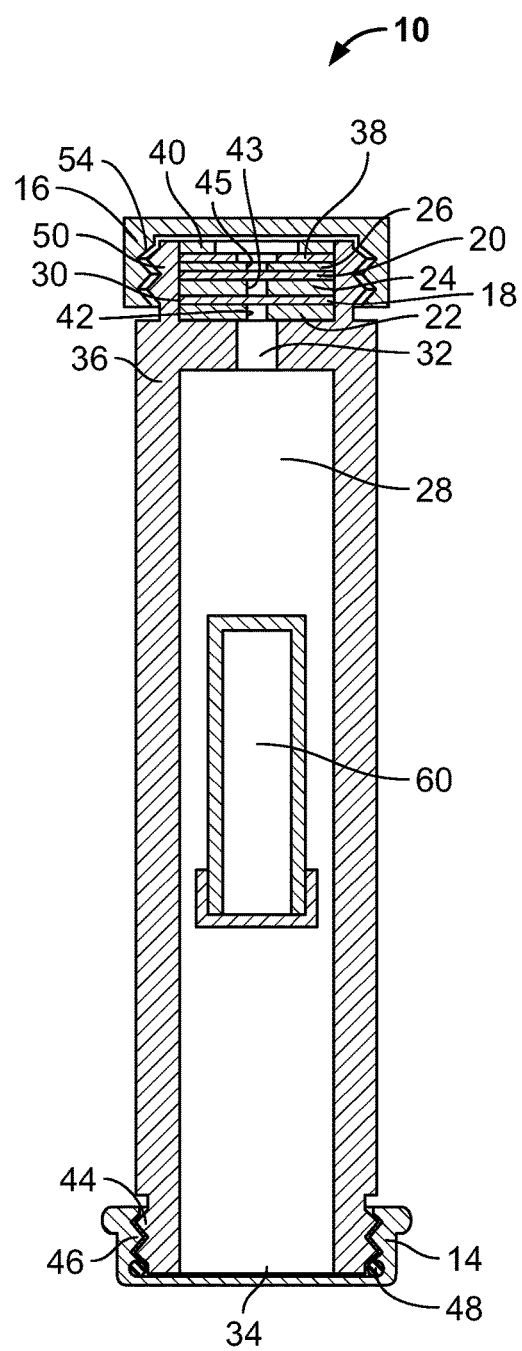
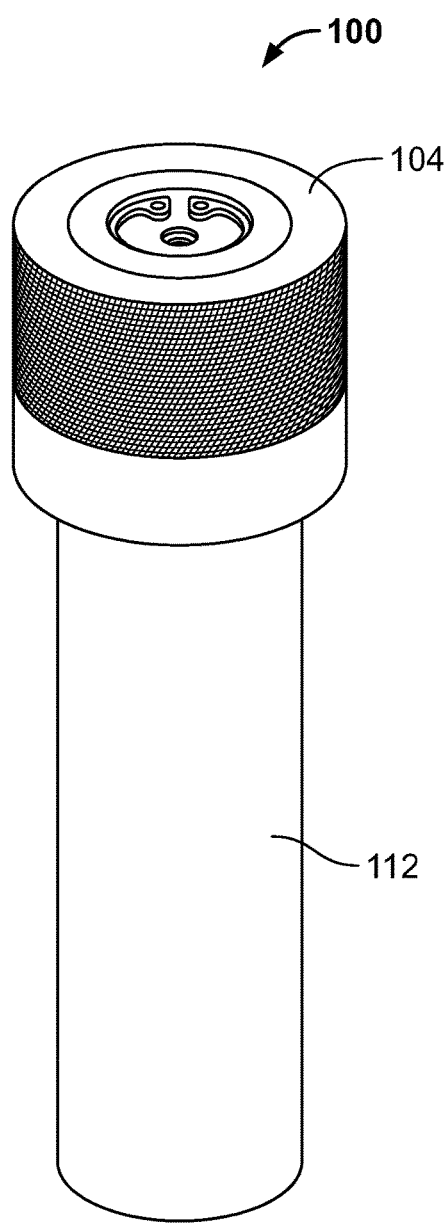
FIG. 3
FIG. 4

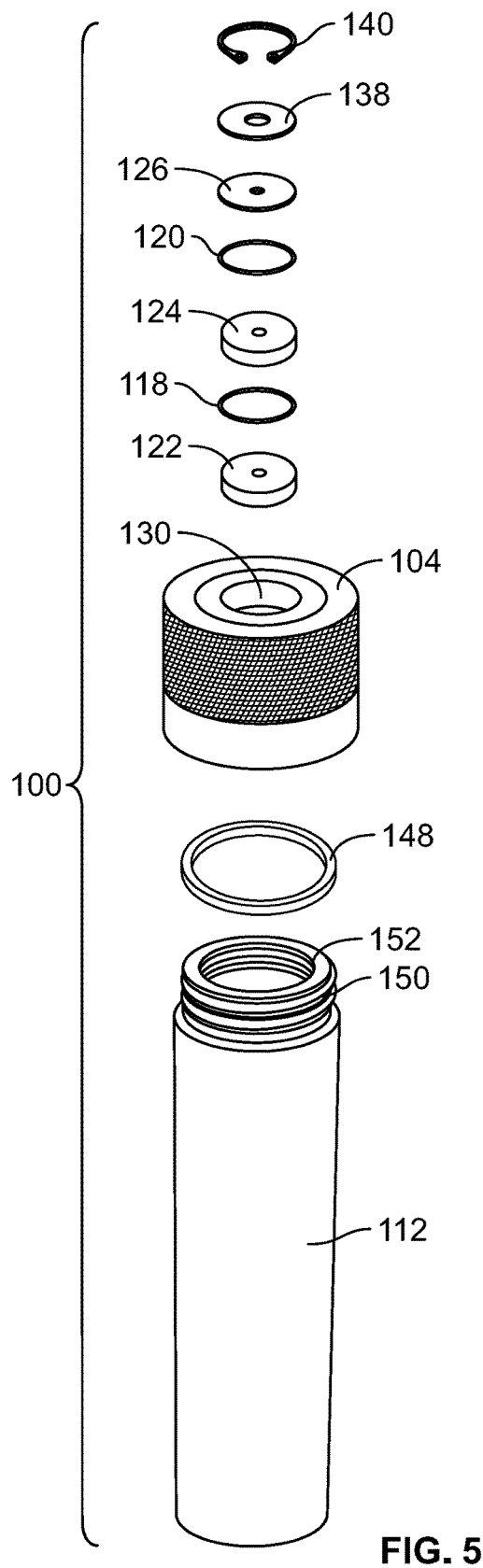
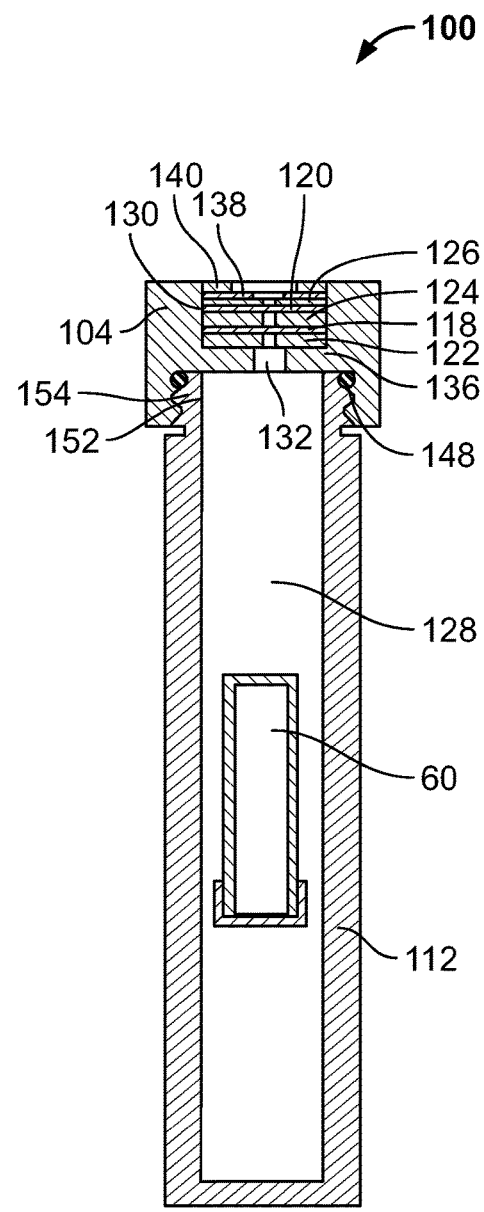
FIG. 5
FIG. 6

STERILIZATION PROCESS CHALLENGE DEVICE

BACKGROUND

The present invention is directed to a sterilization process challenge device for verifying the efficacy of a sterilization process.

The sterilization of medical equipment, towels (for hospital and operating room use), gowns and the like is carried out, for the most part, using steam sterilization equipment and methods. For example, a bundle of towels is placed into a steam sterilizer, a vacuum is drawn in the sterilizer to evacuate the air, and steam is introduced to sterilize the bundle of towels.

Due to the nature of the towels being "bundled" it may be difficult to assure that the innermost regions (volume) of the towels have been sufficiently subjected to the steam (time and temperature) to assure proper levels of sterilization. Essentially, it is a "challenge" for the steam to be introduced to the innermost parts to effect sterilization.

To this end, "challenge packs" or "challenge kits" have been developed to simulate the bundle and more specifically to simulate the difficulty or resistance in reaching the innermost parts: (1) to effect a vacuum; and (2) to introduce steam sufficient to sterilize the local area. There is in fact an ANSI standard for challenge packs that is based upon a bundle of towels having a specific size.

Presently, there are challenge packs on the market. These include paper stacks (stacked like a deck of cards) with an indicator sheet generally in the middle of the stack that can indicate either that a vacuum has been achieved or that a sufficient amount of steam has reached the indicator pack. Another includes a paper stack with a cut out center with a biological indicator vile in the middle. Still another type of indicator includes a plastic tube that has a hole in one end, is packed with a permeable material (such as a towel or absorbent paper sheet) and an indicator at the opposite end.

U.S. Pat. No. 9,017,994, which is assigned to the Applicant of the present application and incorporated herein by reference, discloses a sterilization test pack including a biological indicator and a chemical indicator. The sterilization test pack also includes at least one external channel providing a restricted flow path(s) to the biological and chemical indicators, in which the at least one channel is defined by a groove(s) or indentation(s) having a depth, a width, and a length. Further, U.S. Pat. No. 7,790,105, which is also assigned to the Applicant of the present application and incorporated herein by reference, discloses a sterilization challenge specimen holder including a holder configured to hold a sterilization indicator, such as a biological indicator, and a plug including grooves configured to provide a restricted flow path(s) to the sterilization indicator.

Accurate and cost effective verification of sterilization processes is important for obvious reasons. The present disclosure provides a cost effective sterilization process challenge device that closely mimics the challenge to reach the innermost regions of a bundle of towels used in the ANSI/AAMI ST79 for sterilization challenge packs.

BRIEF SUMMARY

In one aspect, a sterilization challenge device for verifying the efficacy of a sterilization process comprises a body including at least one chamber configured to contain at least one sterilization indicator and a filter assembly including at least one filter member. The only fluid communication between the at least one chamber and an external environment is provided through the filter assembly.

In some embodiments, the filter assembly may also include at least one gasket including an opening. In such embodiments, the at least one filter member and the at least one gasket may be arranged, such that each of the filter member is adjacent at least one gasket, and when the filter assembly includes two or more filter members, is separated from each other by at least one gasket. For example, the filter assembly may include one filter member arranged between two gaskets, two or more filter members, each of which is separated from each other by at least one gasket.

In an embodiment, the body may be a tubular body including a first chamber configured to hold at least one sterilization indicator and a second chamber configured as the filter assembly including at least one filter member. The tubular body may include a first opening at one end, a second opening at an opposite end, and a wall therebetween. The first chamber may be defined between the first opening and the wall, while the second chamber is defined between the second opening and the wall. In such an embodiment, the first chamber and the second chamber may be arranged adjacent each other separated by the wall. The wall may include an opening to provide a flow path between the first and second chambers.

In some embodiments, the second chamber may include at least two filter members, each of which is separated by a gasket having an opening. For example, the second chamber may include two filter members and three gaskets, each of the gaskets having an opening. A first gasket may be arranged in the bottom of the second chamber adjacent the wall followed by a first filter member, a second gasket, a second filter member, and a third gasket. In such an embodiment, the only flow path into the first chamber from an external environment may be provided through the opening of the third gasket, the second filter member, the opening of the second gasket, the first filter member, the opening of the first gasket, and the opening in the wall. The second chamber may also include a washer and a resilient retaining ring arranged over the third gasket to secure the filter members and the gaskets in the second chamber. The first chamber may contain a biological indicator and/or a chemical indicator.

In an embodiment, the sterilization challenge device may include a cap configured to engage the tubular body proximate the first opening to close the first opening. In such an embodiment, the tubular body may include an external thread proximate the first opening, and the cap may include an internal thread configured to mate with the external thread. Further, a sealing member may be provided between the cap and the tubular body to provide a fluid-tight closure of the first opening when the tubular body is closed with the cap.

The sterilization challenge device may also include a second cap configured to engage the tubular body proximate the second opening. The tubular body may include an external thread proximate the second opening, and the second cap may include an internal thread configured to mate with the external thread. The threads may be configured such that a gaseous sterilization medium may flow therebetween to enter the second chamber when the tubular body is closed with the second cap.

In some embodiments, the body may be a tubular body that is closed at one end, and includes an opening at an opposite end and a single chamber defined therebetween. The filter assembly may be provided in a cap assembly configured to engage the tubular body proximate the opening. The cap assembly may include a top portion including a second chamber and a bottom portion configured to engage the tubular body.

In an embodiment, the top and bottom portions of the cap assembly may be arranged adjacent each other separated by a wall therebetween. The second chamber may include at least two filter members, the filter members being separated from each other with a gasket therebetween. For example, the second chamber may include two filter members and three gaskets, each of the gaskets having an opening. A first gasket may be arranged in the bottom of the second chamber adjacent the wall followed by a first filter member, a second gasket, a second filter member, and a third gasket. The wall may include an opening, such that the only flow path between the first chamber and the external environment is provided through the opening of the third gasket, the second filter member, the opening of the second gasket, the first filter member, the opening of the first gasket, and the opening in the wall when the tubular body is closed with the cap assembly. The second chamber may also include a washer and a resilient retaining ring arranged over the third gasket to secure the filter members and the gaskets in the second chamber. The first chamber defined in the tubular body may contain a biological indicator and/or a chemical indicator.

In another embodiment, the cap assembly may include a top wall including an opening, wherein the second chamber is defined adjacent the top wall and between the top wall and the bottom portion. The second chamber may include two filter members and three gaskets, each of the gaskets having an opening. In such an embodiment, a first gasket may be arranged adjacent the top wall followed by a first filter member, a second gasket, a second filter member, and a third gasket, wherein the only flow path into the first chamber from the external environment is provided through the opening in the top wall, the opening of the first gasket, the first filter member, the opening of the second gasket, the second filter member, and the opening of the third gasket.

The tubular body may include a first thread proximate the opening, and the bottom portion of the cap assembly may include a second thread configured to mate with the first thread. Further, a sealing member may be provided between the cap assembly and the tubular body for a fluid-tight closure when the tubular body is closed with the cap assembly.

In another aspect, a sterilization challenge device comprises a tubular body including a first chamber configured to contain at least one sterilization indicator, a second chamber configured to include at least one filter member, and a flow path therebetween. The only fluid communication between the first chamber and an external environment may be provided through the second chamber. The tubular body may include a first opening at one end, a second opening at an opposite end, and a wall therebetween. The first chamber may be defined between the first opening and the wall, and the second chamber may be defined between the second opening and the wall, such that the first and second chambers are arranged adjacent each other separated by the wall. The flow path between the first and second chambers may be defined by an opening in the wall.

In an embodiment, the second chamber may include at least two filter members and at least two gaskets, each of which having an opening. The filter members may be arranged in the second chamber separated from each other with a gasket therebetween. The only fluid flow path from the external environment into the first chamber may be provided through the at least two filter members, openings of the at least two gaskets, and the opening in the wall. The sterilization challenge device may also include a first cap configured to engage the tubular body proximate the first opening to provide a fluid-tight closure of the first opening.

In yet another aspect, a sterilization challenge device may comprise a tubular body including a chamber and a cap assembly. The tubular body may have a closed bottom and include an opening at an opposite end with the chamber defined therebetween. The chamber may be configured to contain at least one sterilization indicator. The cap assembly may comprise a top portion including a second chamber configured to contain at least one filter member, a bottom portion configured to engage the tubular body proximate the opening, and a wall including an opening. The only fluid communication between the first chamber and an external environment may be provided through the second chamber of the cap assembly.

In an embodiment, the second chamber defined in the cap assembly may include at least one filter member and at least one gasket including an opening. The first chamber defined in the tubular body may contain a biological indicator and/or a chemical indicator. The only flow path between the external environment and the first chamber when the tubular body is closed with the cap assembly may be provided through the opening in the at least one gasket, the at least one filter member, and the opening in the wall.

Other aspects, objectives and advantages will become more apparent from the following detailed description.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein:

FIG. 3 is a cross sectional view of the challenge device of FIG. 1;

FIG. 4 is a perspective view of a sterilization process challenge device according to another embodiment;

FIG. 5 is an exploded view of the challenge device of FIG. 4;

FIG. 6 is a cross sectional view of the challenge device of FIG. 4;

For simplicity and clarity of illustration, elements shown in the figures may not be drawn to scale. For example, the dimension of some of the elements may be exaggerated relative to each other for clarity.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

It should be further understood that the title of this section of this specification, namely, "Detailed Description Of The Invention", relates to a requirement of the United States Patent Office, and does not imply, nor should be inferred to limit the subject matter disclosed herein.

A sterilization process challenge device according to various embodiments is provided. The challenge device may be configured to hold a biological indicator and/or a chemical indicator to test the efficacy of a sterilization process. For example, the challenge device may be used to verify the efficacy a sterilization process involving steam or gaseous sterilization medium/sterilants, such as gaseous hydrogen peroxide, gaseous ethylene oxide, and the like.

The challenge device may be configured to hold a biological indicator, which may contain microorganisms, such as *Escherichia coli, Legionella* sp., *Campylobacter* sp., *Staphylococcus, Streptococcus* species and *Cryptosporidium,* and/or a chemical indicator for verifying the efficacy of a sterilization process.

Figure 1:
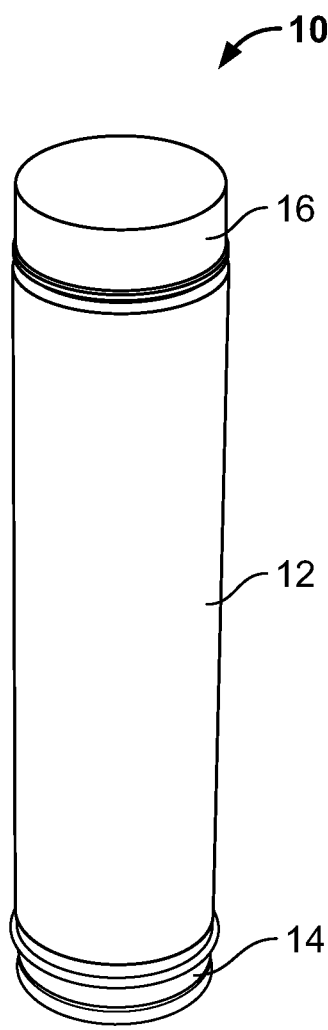
FIG. 1 is a perspective view of a sterilization process challenge device according to an embodiment.
Figure 2:
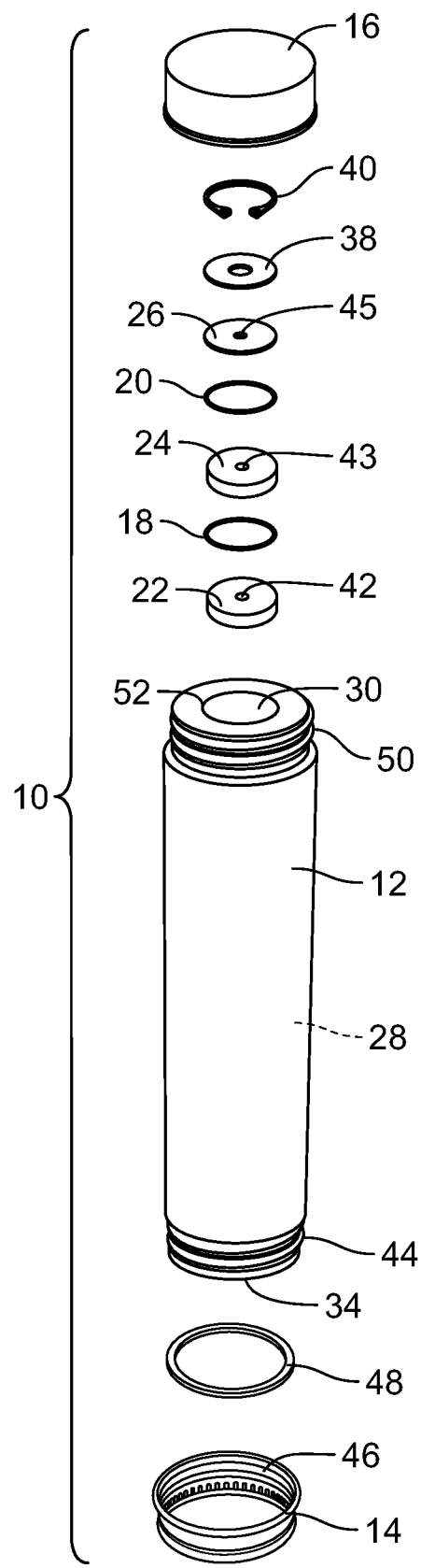
FIG. 2 is an exploded view of the challenge device of FIG. 1.

FIGS. 1-3 illustrate a sterilization process challenge device 10 according to an embodiment. The challenge device 10 may generally comprise a tubular body 12, caps 14, 16, a plurality of filter members 18, 20, and a plurality of gaskets 22, 24, 26. The tubular body 12 may include a first chamber 28 configured to hold a biological indicator and/or chemical indicator, a second chamber 30 configured to hold the plurality of filter members 18, 20 and the plurality of gaskets 22, 24, 26, and a flow path 32 therebetween. In this embodiment, the challenge device 10 includes the tubular body 12 having a generally cylindrical shaped body. In other embodiments, the challenge device may include a body comprising at least one chamber for holding a biological indicator and/or chemical indicator, which may be provided in various shapes, such as generally rectangular, triangular, etc.

The first cap 14 may be configured to engage a peripheral portion of the tubular body 12 to close and seal an opening 34 of the first chamber 28, such that an only fluid flow path from the external environment into the first chamber 28 may be provided through the second chamber 30 containing the plurality of filter members 18, 20 and the plurality of gaskets 22, 24, 26, and through the flow path 32 between the first and second chambers 28, 30.

The first and second chambers 28, 30 may be arranged side by side, separated by a wall 36 including the flow path 32 defined by an opening therein. The first chamber 28 may be configured as a larger chamber for holding a biological indicator and/or chemical indicator. For example, the first chamber 28 may contain a biological indicator 60, such as a self-contained biological indicator (SCBI) and/or a chemical indicator. The second chamber 30 may be configured as a relatively smaller chamber for holding the plurality of filter members 18, 20 and the plurality of gaskets 22, 24, 26, which may be arranged and configured to restrict a flow of steam or a gaseous sterilization medium to the first chamber 28.

In the embodiment of FIGS. 1-3, the challenge device 10 includes two filter members 18, 20 and three gaskets 22, 24, 26. Each of the filter members 18, 20 and the gaskets 22, 24, 26 may be configured to have a generally circular shape to fit inside the second chamber 30 having a generally circular cross section. The filter members 18, 20 may be arranged such that each of the filter members 18, 20 is separated by at least one gasket. For example, a first gasket 22 may be arranged in the bottom of the second chamber 30 followed by a first filter member 18, a second gasket 24, a second filter member 20, and a third gasket member 26 as shown in FIGS. 2 and 3. An optional washer 38 and an optional resilient retaining ring 40 may be arranged over the third gasket 26 to secure the filter members 18, 20 and the gasket members 22, 24, 26 in the second chamber 30. In other embodiments, the challenge device 10 may include one filter member or more than two filter members, each of which is separated by at least one gasket. For example, the challenge device 10 may include one filter member arranged between two gaskets, or may include three filter members and four gaskets, wherein each of the filter members is arranged between adjacent gaskets.

The plurality of filter members 18, 20 may be formed from a suitable filter material having a micron rating of about 1.0 to about 4 micron, preferably about 1.5 to 2.5 micron. Examples of the suitable filter material include, but are not limited to, a binder-free microfiber glass filter having a micron rating of 1.0, such as Ahlstrom™ Grade 121, an ashless, cotton filter having a micron rating of 1.5, such as Ahlstrom™ Grade 94, a white, smooth surface, cotton filter having a micron rating of 1.5, such as Ahlstrom™ Grade 610, a white, smooth surface, cotton filter having a micron rating of 2.0, such as Ahlstrom™ Grade 642, a white, smooth surface, cotton filter having a micron rating of 2.5, such as Ahlstrom™ Grade 601, and a white, smooth surface, cotton filter having a micron rating of 3.0, such as Ahlstrom™ Grade 238.

Each of the gaskets 22, 24, 26 may include an opening 42, 43, 45 to provide a flow path through the gasket. In an embodiment, each of the gaskets 22, 24, 26 may be provided with a generally circular opening 42, 43, 45 having a diameter of about 1/32 to 1/4 inch, preferably about 1/16 to about 5/32 inch, and more preferably about 3/32 inch, extending through the thickness of the gasket. The plurality of the gasket may be formed from a suitable sealing material, such as rubber, silicone, polymer and the like. A micron rating of filter members, a number of filter members, and/or a size of an opening of gaskets may be varied to adjust a flow resistance from the external environment into the first chamber 28.

The bottom opening 34 of the first chamber 28 may be closed fluid-tight with the first cap 14. In an embodiment, the tubular body 12 may be provided with an external thread 44 proximate the opening 34, and the first cap 14 may be provided with an internal thread 46 configured to engage with the external thread 44 to close the opening 34. A seal 48, such as the O-ring illustrated in FIGS. 2 and 3 may be fitted in the first cap 14 to provide a gas-tight seal between the first cap 14 and the tubular body 12.

The challenge device 10 may also include an option second cap 16 for closing the second chamber 30 as shown in FIGS. 1-3. In such an embodiment, the tubular body 13 may be provided with an external thread 50 proximate an opening 52 of the second chamber 30, and the second cap 16 may be provided with an internal thread 54 configured to engage with the external thread 50 to close the opening 52, while allowing steam or a gaseous sterilization medium to flow therebeween. In another embodiment, the filter members 18, 20 and gasket members 22, 24, 26 may be secured in place with the washer 38 and the resilient retaining ring 40 without a second cap.

The tubular body 12 may be formed from a suitable polymeric material, such as polypropylene, polycarbonate, polyester, polyolefin, polystyrene, polyacrylamide, polymethacrylate, poly(methyl)methacrylate, polyimide, polyethylene terephthalate, polybutylene terephthalate, polyvinylchloride, or other similar polymers. In an embodiment, the tubular body 12 is formed from polypropylene.

In an embodiment, the challenge device 10 may include a chemical indicator and be configured such that the chemical indicator is visible from outside to allow a user may check the chemical indicator without removing the first cap 14. In such an embodiment, the tubular body 12 may be formed from a clear plastic material to facilitate viewing of the chemical indicator from outside the challenge device 10.

In use, the challenge device 10 may be placed in a sterilization chamber along with the objects to be sterilized. During a sterilization process, steam or other gaseous sterilization medium may flow into the second chamber 30 through a gap between the second cap 16 and the tubular body 12, and through the openings in the washer 38 and gaskets 22, 24, 26, and through the filter papers 18, 20, wherein the flow of the gaseous sterilization medium is restricted. The gaseous sterilization medium may then flow through the flow path 32 into the first chamber 28 and permeate into the biological and/or chemical indicators. At the end of the sterilization process, a user may open the first cap 14 to remove the biological and/or chemical indicators. The challenge device 10 may be configured such that the steam or other gaseous sterilization medium may enter the first chamber 28 through the second chamber 30, wherein the plurality of filter elements 18, 20 and the plurality of gaskets 22, 24, 26 are arranged and configured to provides a restrictive flow path for the steam or other gaseous sterilization medium that closely mimic the restrictive flow path into the center of 16-towel test pack used in the ANSI/AAMI ST79 for sterilization challenge packs. During some sterilization processes, a vacuum may be drawn in the sterilization equipment (and thus in the sterilization challenge device 10), following which the sterilization medium is introduced into the equipment (and thus the challenge device 10.)

FIGS. 4-6 illustrate a sterilization process challenge device 100 according to an embodiment. The challenge device 100 may be similarly configured to the challenge device 10 of FIGS. 1-3, generally comprising a tubular body 112, a plurality of filter members 118, 120, and a plurality of gaskets 122, 124, 126. In this embodiment, the tubular body 112 may be closed at one end and include an opening 152 at the other end, wherein a single chamber 128 is defined therebetween for holding a biological indicator 60 and/or chemical indicator. The plurality of filter members 118, 120 and the plurality of gaskets 122, 124, 126 may be arranged in a cap assembly 104 configured to engage the tubular body 112 proximate the opening 152.

The cap assembly 104, which may also be referred to as a filter assembly herein, may include a top portion including a chamber 130 and a bottom portion configured to engage the tubular body 112. The chamber 130 may be configured to hold the plurality of filter members 118, 120 and the plurality of gaskets 122, 124, 126, and a flow path 132. Each of the filter members 118, 120 and the gaskets 122, 124, 126 may be configured to have a generally circular shape to fit inside the chamber 130 having a generally circular cross section. The filter members 118, 120 may be arranged such that each of the filter members 118, 120 is separated by at least one gasket. For example, a first gasket 122 may be arranged in the bottom of the chamber 130 followed by a first filter member 118, a second gasket 124, a second filter member 120, and a third gasket member 126 as shown in FIGS. 5 and 6. A washer 138 and a resilient retaining ring 140 may be arranged over the third gasket 126 to secure the filter members 118, 120 and the gasket members 122, 124, 126 in the chamber 130. In other embodiments, the challenge device 100 may include one filter member or more than two filter members, each of which is separated by at least one gasket.

The bottom portion of the cap assembly 104 may include an internal thread 154 configured to mate with an external thread 152 of the tubular body 112 provided proximate the opening 152. The flow path 132 may be defined by an opening in a bottom wall 136 of the cap assembly 104 and configured to provide fluid communication between the chamber 130 of the cap assembly 104 and the chamber 128 of the tubular body 112 when the cap assembly 104 is engaged with the tubular body 112. A sealing member 148 may be provided to create a fluid-tight closure between the cap assembly 104 and the tubular body 112, such that the only flow path into the chamber 128 of the tubular body 112 from an external environment is through the chamber 130 of the cap assembly 130 including the plurality of filter members 118, 120 and the plurality of gaskets 122, 124, 126, and through the flow path 132.

Figure 7:
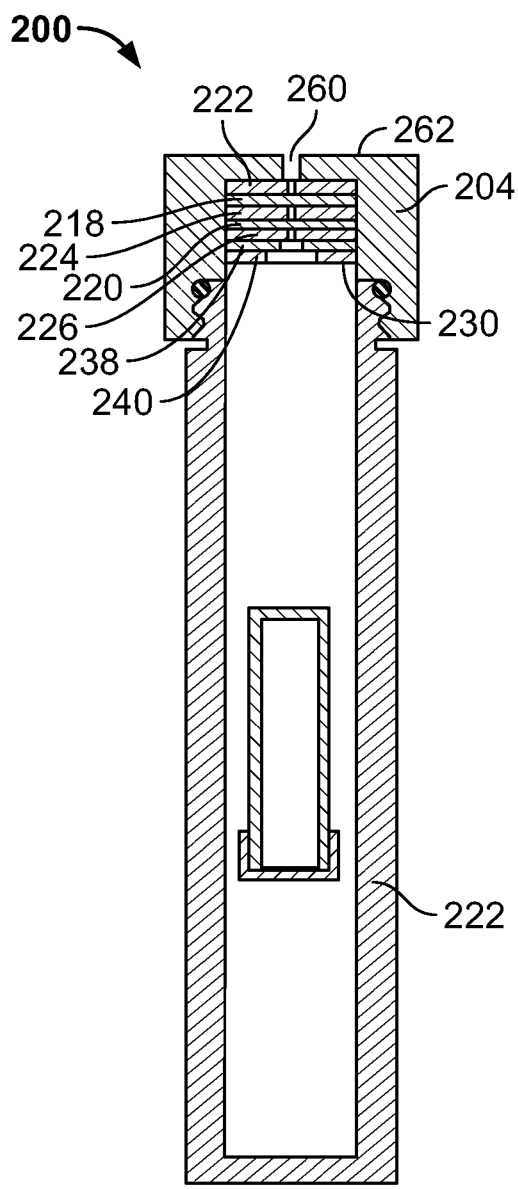
FIG. 7 is a cross sectional view of a challenge device according to yet another embodiment.

FIG. 7 is a cross sectional illustration of a sterilization process challenge device 200 according to another embodiment. The challenge device 200 may be similarly configured to the challenge device 100 of FIGS. 4-6, generally comprising a tubular body 222 and a cap assembly 204 including filter members 218, 220, gaskets 222, 224, 226, a washer 238, and a resilient retaining ring 240. In this embodiment, the cap assembly 204 is configured such that a chamber 230 may be accessible from bottom and includes a relatively small opening 260 defined through a top wall 262 to provide a fluid path into the chamber 230.

Figure 8:
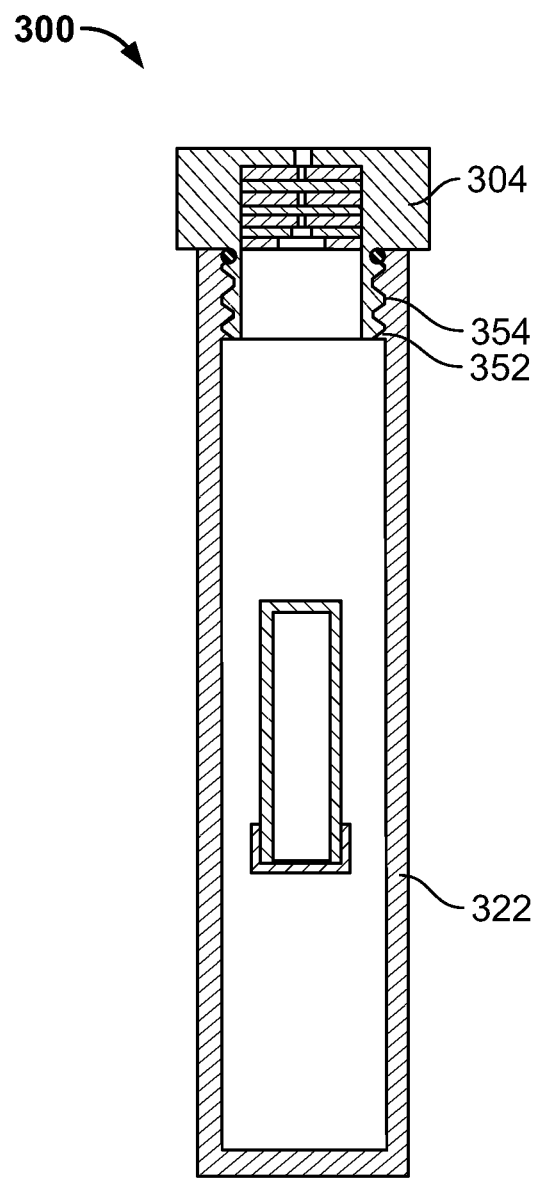
FIG. 8 is a cross sectional view of a challenge device according to an embodiment.

FIG. 8 is a cross section illustration of a sterilization process challenge device 300 according to yet another embodiment. The challenge device 300 may be similarly configured to the challenge device 200, generally comprising a tubular body 322 and a cap assembly 304. In this embodiment, the tubular body 322 may include an internal thread 352, and the cap assembly 304 may include an external thread 354 configured to mate with the internal thread 352 when a bottom portion of the cap assembly 304 is inserted into the tubular body 322.

Some prior art challenge packs include an absorber or other sterilant-reactive device to restrict the flow of gaseous sterilization medium into the chambers containing biological and/or chemical indicators. The challenge device according to various embodiments of the present disclosure may be configured to provide the restrictive flow path that closely mimics the flow path to the center of 16-towel pack without requiring an absorber or other similar devices for further restricting flow of the gaseous sterilization medium.

Sterilization process challenge device samples configured according to the embodiments disclosed in the present disclosure including two filter members having a micron rating of about 1.5 micron and three gaskets, each including an opening having a diameter of about 3/32 inch, were tested in various autoclave cycles. Test results showed positive biological activity (live biological activity) at least up to 2 min of sterilization cycles indicating that the sterilization process challenge device samples provided sufficient flow resistance to mimic the flow resistance to the center of 16-towel pack.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A sterilization challenge device, comprising:
a body including at least one chamber configured to contain at least one sterilization indicator; and
a filter assembly including a filter member and two gaskets, each gasket having an opening, the filter member and the gaskets being in stacked relationship to one another with the filter member disposed between the two gaskets, the filter assembly positioned in the body;
wherein the sterilization challenge device has a single opening for the flow of gaseous sterilant into the at least one chamber and for flow out of the at least one chamber to draw a vacuum in the chamber, wherein the only fluid communication between the at least one chamber and an external environment is provided through the single opening and the filter assembly, wherein the filter member and the gaskets are configured to provide a restrictive flow path into the at least one chamber for a gaseous sterilization medium, and wherein the flow out of the at least one chamber is to draw a vacuum in the at least one chamber and the flow into the at least one chamber is for the inlet of the gaseous sterilization medium.

2. The sterilization challenge device of claim 1, wherein the body is a tubular body including a first chamber configured to hold the at least one sterilization indicator and a second chamber configured to hold the filter assembly.

3. The sterilization challenge device of claim 2, wherein the tubular body includes a first opening at one end, a second opening at the other end, and a wall therebetween, wherein the first chamber is defined between the first opening and the wall, and the second chamber is defined between the second opening and the wall, such that the first and second chambers are arranged adjacent each other separated by the wall, wherein the wall includes an opening to provide a flow path between the first and second chambers.

4. The sterilization challenge device of claim 1, wherein the first chamber contains a biological indicator and/or a chemical indicator.

5. The sterilization challenge device of claim 3, further including a first cap configured to engage the tubular body proximate the first opening to close the first opening and a second cap configured to engage the tubular body proximate the second opening, wherein the tubular body includes a first external thread proximate the first opening, and the first cap includes a first internal thread configured to mate with the first external thread, wherein a sealing member is provided between the first cap and the tubular body to provide a fluid-tight closure of the first opening when the first cap and the tubular body are engaged, wherein the tubular body includes a second external thread proximate the second opening, and the second cap include a second internal thread configured to mate with the second external thread, wherein the second internal and external threads are configured to allow a gaseous sterilization medium to flow through therebetween to enter the second chamber when the tubular body is closed with the second cap.

6. The sterilization challenge device of claim 1, wherein the body is a tubular body closed at one end, and includes an opening at an opposite end and wherein the filter assembly is provided in a cap assembly configured to engage the tubular body proximate the opening.

7. The sterilization challenge device of claim 6, wherein the cap assembly includes a top portion including a second chamber and a bottom portion configured to engage the tubular body, wherein the second chamber includes the filter assembly, and wherein the first chamber contains a biological indicator and/or a chemical indicator.

8. The sterilization challenge device of claim 7, wherein the top portion and the bottom portion are arranged adjacent each other and separated by a wall therebetween, wherein the second chamber includes the filter member and the two gaskets, wherein the filter member includes a first filter member and a second filter member, and further including a third gasket, wherein each of the first, second, and third gaskets has an opening, wherein the first gasket is arranged in the bottom of the second chamber adjacent the wall followed by the first filter member, the second gasket, the second filter member, and the third gasket, wherein the wall includes an opening, such that the only flow path into the first chamber from the external environment is provided through the opening of the third gasket, the second filter member, the opening of the second gasket, the first filter member, the opening of the first gasket, and the opening in the wall.

9. The sterilization challenge device of claim 7, wherein the cap assembly includes a top wall including an opening, wherein the second chamber is defined adjacent the top wall and between the top wall and the bottom portion, wherein the second chamber includes the filter member and the two gaskets, wherein the filter member includes a first filter member and a second filter member, and further including a third gasket, wherein each of the first, second, and third gaskets has an opening, wherein the first gasket is arranged adjacent the top wall followed by the first filter member, the second gasket, the second filter member, and the third gasket, wherein the only flow path into the first chamber from the external environment is provided through the opening in the top wall, the opening of the first gasket, the first filter member, the opening of the second gasket, the second filter member, and the opening of the third gasket.

10. The sterilization challenge device of claim 7, wherein the tubular body includes a first thread proximate the opening, and the bottom portion of the filter assembly includes a second thread configured to mate with the first thread, wherein a sealing member is provided between the cap assembly and the tubular body to provide a fluid-tight closure of the first opening when the tubular body is closed with the cap assembly.

11. A sterilization challenge device comprising a tubular body including a first chamber configured to contain at least one sterilization indicator, and a second chamber configured to include a filter member and two gaskets, the filter member and the gaskets being in stacked relationship to one another with the filter member disposed between the two gaskets, each gasket including an opening, and a flow path therebetween, wherein the sterilization challenge device has a single opening for the flow of sterilant into the first chamber and for flow out of the first chamber, wherein the only fluid communication between the first chamber and an external environment is provided through the second chamber, wherein the filter member and the gaskets are configured to provide a restrictive flow path into the first chamber for a gaseous sterilization medium.

12. The sterilization challenge device of claim 11, wherein the tubular body includes a first opening at one end, a second opening at the other end, and a wall therebetween, wherein the first chamber is defined between the first opening and the wall, and the second chamber is defined between the second opening and the wall, such that the first and second chambers are arranged adjacent each other separated by the wall, wherein the flow path between the first and second chambers is defined by an opening in the wall.

13. The sterilization challenge device of claim 12, further including a first cap configured to engage the tubular body proximate the first opening to provide a fluid-tight closure of the first opening.

14. A sterilization challenge device, comprising:
a tubular body including a closed bottom, and an opening at an opposite end, and a first chamber defined therebetween configured to contain at least one sterilization indicator; and
a cap assembly comprising a top portion including a second chamber configured to contain a filter member and two gaskets, the filter member and the two gaskets being in stacked relationship to one another with the filter member disposed between the two gaskets, the second chamber having a bottom portion configured to engage the tubular body proximate the opening;
wherein the sterilization challenge device has a single opening for flow of sterilant into the at least one chamber and for flow out of the at least one chamber and wherein the only fluid communication between the first chamber and an external environment is provided through the second chamber of the cap assembly, wherein the at filter member and the two gaskets are configured to provide a restrictive flow path into the first chamber for a gaseous sterilization medium.

15. The sterilization challenge device of claim 14, wherein the cap assembly comprises a wall including an opening, wherein the first chamber defined in the tubular body contains a biological indicator and/or a chemical indicator, wherein the only flow path from the external environment into the first chamber when the cap assembly is engaged with the tubular body is provided through the two gaskets, the filter member and the opening in the wall.

* * * * *